United States Patent [19]

Swanson

[11] Patent Number: 5,465,147
[45] Date of Patent: Nov. 7, 1995

[54] METHOD AND APPARATUS FOR ACQUIRING IMAGES USING A CCD DETECTOR ARRAY AND NO TRANSVERSE SCANNER

[75] Inventor: Eric A. Swanson, Acton, Mass.

[73] Assignee: Massachusetts Institute of Technology, Cambridge, Mass.

[21] Appl. No.: 253,059

[22] Filed: Jun. 2, 1994

Related U.S. Application Data

[63] Continuation-in-part of Ser. No. 875,670, Apr. 29, 1992, Pat. No. 5,321,501, which is a continuation-in-part of Ser. No. 692,877, Apr. 29, 1991, abandoned.

[51] Int. Cl.[6] .................................................. G01B 9/02
[52] U.S. Cl. ........................ 356/345; 356/349; 356/360
[58] Field of Search ................................... 356/345, 349, 356/359, 360

[56] References Cited

U.S. PATENT DOCUMENTS

| | | | |
|---|---|---|---|
| 5,007,711 | 4/1991 | Morris et al. | 380/486 |
| 5,033,853 | 7/1991 | Frangineas, Jr. | 356/346 |
| 5,202,745 | 4/1993 | Sorin et al. | 356/73.1 |
| 5,268,741 | 12/1993 | Chou et al. | 356/73.1 |
| 5,321,501 | 6/1994 | Swanson et al. | 356/345 |
| 5,365,335 | 11/1994 | Sorin | 356/73.1 |

OTHER PUBLICATIONS

David Huang, et al., "Optical coherence tomography" Reports, (science) vol. 254, pp. 1178–1181 (Nov. 1991).

Primary Examiner—Samuel A. Turner
Assistant Examiner—Robert Kim
Attorney, Agent, or Firm—Weingarten, Schurgin, Gagnebin & Hayes

[57] ABSTRACT

An apparatus and method for acquiring an at least one dimensional digital image of a region of an object using an optical source which outputs a first optical beam having a short coherence length. A splitter splits the first optical beam into a reference beam and an object beam. The reference beam travels to a reference scatterer and the object beam is directed toward the region of the object. An array detector such as a charge coupled device receives a portion of the object beam and a portion of the reference beam and detects the resulting incident intensity over the at least one dimension and outputs a signal. Since the coherence length of the source is short, the signal output from the detector array corresponds to one or more dimensional slice of the object which represents the above region.

33 Claims, 6 Drawing Sheets

METHOD AND APPARATUS FOR ACQUIRING IMAGES USING A CCD DETECTOR ARRAY AND NO TRANSVERSE SCANNER

RELATED APPLICATIONS

This application is a continuation-in-part of U.S. patent application Ser. No. 07/875,670 filed on Apr. 29, 1992 U.S. Pat. No. 5,321,501 which in turn was a continuation-in-part of U.S. patent application Ser. No. 07/692,877 filed on Apr. 29, 1991 now abandoned the contents of both of which are incorporated herein by reference.

BACKGROUND OF THE INVENTION

1. Field of the Invention

This invention relates generally to an apparatus and method for acquiring an at least one dimensional image of an object and in particular to an apparatus and method for acquiring a series of at least one dimensional images of an object at high rates using a charge coupled device (CCD) array, whereby each at least one dimensional images are captured in a parallel fashion without requiring any transverse scanning.

2. Description of Related Art

There are many industrial, medical, and other applications where one or two dimensional images of an object are required. In addition, these applications often require both high spatial resolution and high longitudinal resolution (less than 10 micrometers), measurements of distances, thicknesses, and optical properties of the object. The applications can include measurements of biological tissue layers, semiconductors and other applications involving multiple thin layers of material, as well as in the non-destructive testing of small structures such as integrated optical circuits, optical connectors, optical couplers, semiconductor lasers and semiconductor optical amplifiers. Such applications also include various medical applications including laser microsurgery, microscopy and diagnostic instrumentation.

Existing techniques for acquiring one or two dimensional images include scanning laser or confocal microscopes and scanning laser ophthalmoscopes (SLO), provide highly spatially resolved images, for example being able to generate real time video images of the eye with a lateral resolution of a few micrometers. However, the depth resolution of SLOs quickly degrade with decreasing numerical aperture. For example, SLO measurements of the retina through the pupil aperture restrict the depth resolution to roughly 200 microns. SLOs are also expensive, costing in the range of a quarter million dollars.

Optical triangulation offers fairly high resolution, but requires parallel boundaries. Such devices also have relatively poor signal-to-noise ratios and have degraded resolution at greater depths, where numerical aperture is restricted.

Existing techniques for performing such measurements include optical coherence domain reflectometers (OCDR), optical time domain reflectometry (OTDR), ultrasound, scanning laser microscopes, scanning confocal microscopes, scanning laser ophthalmoscopes and optical triangulation. Existing OCDR systems do not normally have the rapid data acquisition rate required for the measurement of biological or other samples having the potential for dynamic movement; while OTDR systems are very expensive and have only limited resolution and dynamic range.

Ultrasound, which is perhaps the most commonly used technique, is disadvantageous for applications such as taking measurements on the eye in that, in order to achieve the required acoustic impedance matches, and to thus avoid beam losses and distortion, contact is generally required between the ultrasonic head or probe and the product or patient being scanned. While such contact is not a problem when scans are being performed on, for example, a patient's chest, such probes can cause severe discomfort to a patient when used for taking eye measurements such as those used for measuring intraocular distances for computing the power of lens implants.

The relatively long wavelengths employed in ultrasound also limit spatial resolution. Further, ultrasound depends on varying ultrasound reflection and absorption characteristics to differentiate and permit recording or display of tissue, or other boundaries of interest. Therefore, when the acoustic characteristics of adjacent layers to be measured are not significantly different, ultrasound may have difficulty in recognizing such boundaries.

A need, therefore, exists for an improved method and apparatus for performing high resolution measurements and in particular for optically performing such measurements, which improved technique does not require contact with the body being measured, which maintains substantially constant high resolution over a scanning depth of interest, regardless of available apertures size and which is relatively compact and inexpensive to manufacture. Such a system should also be capable of providing differentiation between sample layers and be able to provide identification of layer material or of selected..properties thereof. Such a system should also be able to provide one, two and three-dimensional images of a scanned body and should be rapid enough for use in biological and other applications where the sample being measured changes over relatively short time intervals. Finally, it would be desirable if such technique could also provide information concerning the birefringence property and spectral properties of the sample.

U.S. patent application Ser. No. 08/033,194 relates to optical measuring systems which can perform high resolution measurements and provide the above advantages. In particular, these systems can perform such measurements without contacting the object or body being measured. The systems maintain substantially constant high resolution and are relatively compact and inexpensive to manufacture. Such systems are also capable of providing differentiation between sample layers, identification of layer material or of selected properties thereof. The systems also provide measurements at rapid enough rates for use in biological and other applications where the sample being measured changes over relatively short time intervals. In fact, they can even provide information concerning the birefringence property and spectral properties of the sample.

Figure 1:
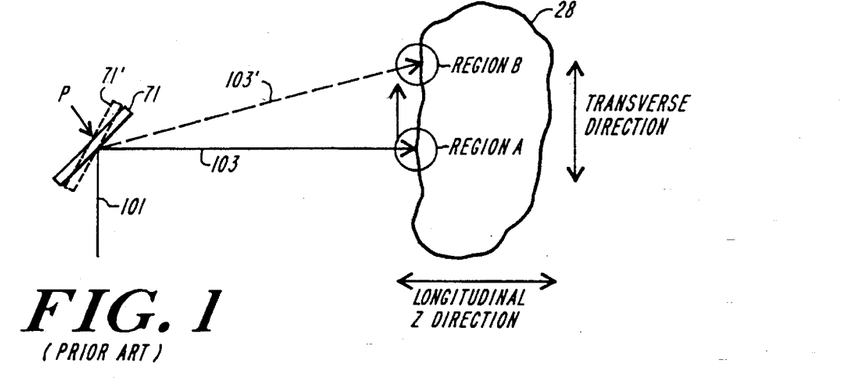
FIG. 1 shows an object being transversely scanned by a beam according to previous methods.

FIG. 1 shows an object 28 being scanned by an optical beam. In particular, a first beam 101 is incident on a scanning mirror 71 which reflects beam 101 as beam 103 which is incident on object 28 at region A. Mirror 71 rotates about pivot P in a controlled manner by some type of rotating driver (not shown) which causes mirror 71 to move to a new position represented by reference numeral 71'. As mirror 71 moves to its new .position, beam 103 scans across object 28 in the transverse direction to region B. As beam 103 passes across object 28, object 28 scatters the radiation back towards some detection unit (not shown) which detects that scattered radiation coherently using radiation from a reference arm (not shown).

The detection unit for capturing a one or two dimensional image of object 28 involves capturing a series of values corresponding to a series of intensity measurements. This series of intensity measurements in turn correspond to a series of regions of object 28 transversely scanned by beam 103 across object 28. Hence, this approach to acquiring measurements across a transverse direction of an object is essentially a serial image capturing process. Consequently, the rate of image capture by such a serial system may be limited by the rate at which individual measurements are acquired and hence at the rate beam 103 is scanned across object 28. This holds regardless of whether or not beam 103 is scanned using a mechanical scanner such as mirror 71 or some other non-mechanical scanning mechanism such as acousto-optic devices. In addition, if a second scanning means such as a second mirror is added to enable scanning in a second transverse direction, the rate of acquisition of resulting two dimensional images is even further reduced.

In some applications, the power of radiation incident on a unit area is fixed, e.g., optical measurements of the human eye.illuminating a human retina. In such cases, simultaneous or parallel illumination and acquisition of information represents a more efficient approach to performing optical measurements than any transverse scanning approach.

Hence it is further desirable to perform a longitudinal scan through an object while acquiring one or two dimensional slices in a completely parallel fashion as the longitudinal scan proceeds. It is desirable to acquire these one or two dimensional images without the use of transverse scanning mirrors which can slow down the rate of image capture and introduce noise which reduce system sensitivity and resolution.

SUMMARY OF THE INVENTION

An object of the invention, therefore, is to provide an apparatus and method of acquiring images of an object in a parallel manner without any transverse scanning across the object.

Another object of the invention is to provide an apparatus and method which can acquire one or two dimensional images at a high rate.

Another object of the invention is to provide an apparatus and method of acquiring a series of two dimensional images along a third direction.

Another object of the invention is to provide an apparatus and method for acquiring one or two dimensional transverse images of an object without having to scan a beam across the object.

Another object of the invention is to provide a relatively inexpensive apparatus and method which can acquire multi-dimensional images.

One advantage of the invention is that it detects a one or two dimensional slice or region of an object without scanning the target radiation over the object.

Another advantage of the invention is that it can output two dimensional images of the object at high rates.

Another advantage of the invention is that it can scan and output a series of two dimensional images of the object along a third direction of the object.

Another advantage of the invention is that it is not limited to capturing regions of the object in the form of a straight line or a flat plane but instead can capture curved lines or curved two dimensional regions of the object.

One feature of the invention is that it uses a source for outputting radiation having a short coherence length.

Another feature of the invention is that it employs heterodyne detection over two dimensions.

Another feature of the invention is that it uses a two dimensional array detector such as a charge coupled device.

Another feature of the invention is that it employs heterodyne detection over the two dimensions of the charge coupled device.

Another feature of the invention is that the charge couple device outputs signals corresponding to two dimensional slices of the object.

These and other objects, advantages and features are accomplished by an apparatus for acquiring an at least one dimensional image of a region of an object without any transverse scanning, including: a source for outputting radiation having a short coherence length; means for splitting the radiation into reference radiation and object radiation; means for receiving the object radiation and directing the object radiation toward the region of the object; means for receiving the reference radiation and directing the reference radiation through a reference path; and array detecting means for receiving a portion of the object radiation scattered off of the region and a portion of the reference radiation, and for detecting incident intensity in a parallel fashion over the at least one dimension resulting from the portion of the reference radiation coherently interfering with the portion of the object radiation scattered from the region and for outputting a signal corresponding to the incident intensity, wherein the portion of the reference radiation requires a reference delay time to travel from the means for splitting to the array detecting means and the portion of the object radiation requires an object delay time to travel from the means for splitting to the region and then to the array detecting means.

The above objects, advantages and features are further accomplished by the provision of the above apparatus, wherein the array detecting means comprises a two dimensional array detecting means for receiving the portion of the object radiation and the portion of the reference radiation, for detecting the incident intensity over two dimensions resulting from the portion of the reference radiation coherently interfering with the portion of the object radiation scattered from the region and for outputting the signal corresponding to the incident intensity.

The above objects, advantages and features are also accomplished by an apparatus for acquiring a two dimensional image of a region of an object, comprising: an optical source for outputting a first optical beam having a short coherence length; means for splitting the first optical beam into a reference beam and an object beam; means for receiving the object beam and directing the object beam toward the region of the object and for collecting a portion of the object beam scattered off of the region; means for receiving the reference beam and directing the reference beam through a reference path; and a two dimensional array detecting means for receiving a portion of the object beam and a portion of the reference beam, for detecting incident intensity over two dimensions resulting from the portion of the reference beam coherently interfering with the portion of the object beam scattered from the region and for outputting a signal corresponding to the incident intensity, wherein the portion of the reference beam requires a reference delay time to travel from the means for splitting to the two dimensional array detecting means and the portion of the object beam requires an object delay time to travel from the means for splitting to the region to the two dimensional array detecting means.

The above and other objects, advantages and features are alternatively accomplished by the provision of a method for acquiring a two dimensional image of a region of an object, comprising the steps of: outputting radiation having a short coherence length; splitting the radiation using a splitter into reference radiation and object radiation; receiving, using an optical guide, the object radiation and directing the object radiation toward the region of the object and for collecting a portion of the object radiation scattered off of the region; receiving the reference radiation and directing the reference radiation through a reference path; receiving a portion of the object radiation and a portion of the reference radiation and detecting incident intensity over two dimensions using a two dimensional array detector resulting from the portion of the reference radiation coherently interfering with the portion of the object radiation scattered from the region; and outputting a signal corresponding to the incident intensity, wherein the portion of the reference radiation requires a reference delay time to travel from the splitter to the two dimensional array detector and the portion of object radiation requires an object delay time to travel from the splitter to the region and back to the two dimensional array detector.

The above and other objects, advantages and features of the present invention will become more apparent from the following description of embodiments thereof taken in conjunction with the accompanying drawings.

DETAILED DESCRIPTION OF THE PREFERRED EMBODIMENTS

Figure 2:
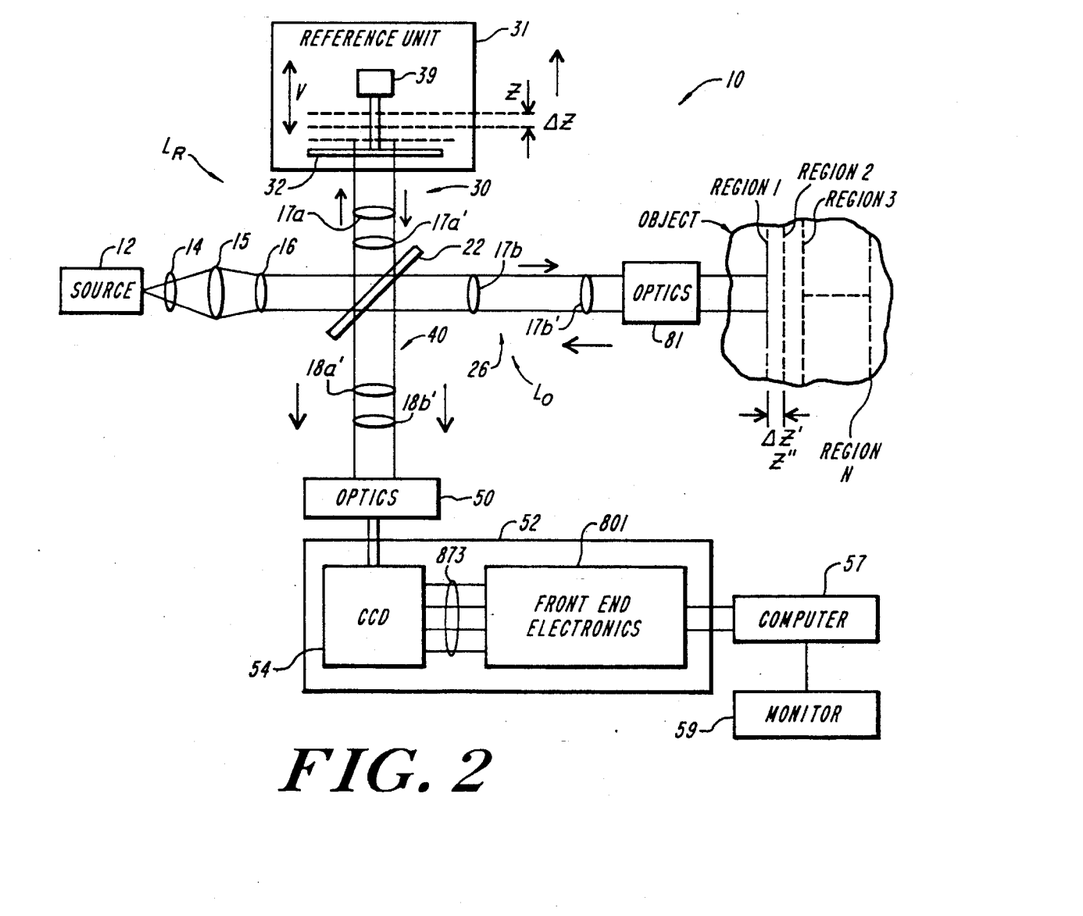
FIG. 2 shows an imaging system according to one embodiment of the invention.

FIG. 2 shows an imaging system 10 according to one embodiment of the invention. In particular, a source 12 outputs radiation with a short coherence length CL outputs radiation 14 which is collimated by collimating lens 15 into collimated radiation 16 which travels toward a splitter 22. A short coherence length CL is a coherence length which is less than the desired longitudinal resolution ($\Delta z'$ in FIG. 2). Collimated radiation 16 can be made elliptical using an anamorphic beam expander or cylindrical lens (i.e., lens 15 can be an anamorphic beam expander or a cylindrical lens) or it can be made more circular (i.e., lens 15 can be a lens with approximately equal power in all transverse directions).

A first portion of radiation 16 referred to here as reference radiation 17a is directed into a reference arm 30 by splitter 22 and a second portion of radiation 16 referred to here as image radiation 17b passes into an image arm 26. Reference radiation 17a travels to a reference unit 31 which includes a reference scatterer 32 and a scanning mechanism 39. A portion of reference radiation 17a is scattered back from reference scatterer 32 toward splitter 22 as radiation 17a'. Image radiation 17b travels to object or sample 28 through optics 81 which can be one or more lenses, a beam expander, a beam contractor or even possibly free space depending on the desired size of beam 17b incident on object 28. A portion of image radiation 17b is scattered back toward splitter 22 as radiation 17b'. A portion of radiation 17a' from reference arm 30 passes through splitter 22 toward a charge coupled device (CCD) array detector 54 as radiation 18a'. The shape of CCD array detector 54 can be made to match that of the collimated radiation. For example, CCD array detector 54 can be a one dimensional CCD array if radiation 16 is elliptical and a two dimensional detector array if radiation 16 is more cylindrical. Likewise, a portion of radiation 17b' from image arm 26 is redirected by splitter 22 toward detector 54 as radiation 18b'.

The path length from splitter 22 to reference scatterer 32 back to splitter 22 and then through to detector 54 will be referred to as the reference path length $L_R$ and the time for radiation 16 to travel the reference path length will be referred to as the reference delay time $T_R$. Similarly, the path length from splitter 22 to object 28 back to splitter 22 and then to detector 54 is the object path $L_O$ and the time for radiation 16 to travel the object path length is the object delay time $T_O$.

The scattered radiation 18b' and 18a' received from object 28 and scatterer 32, respectively, are combined at splitter 22, resulting in interference fringes for length matched reflections (i.e., reflections for which the difference in reflection path lengths is less than the source coherence length) and the resulting combined output is transmitted to optics 50 which can be used to expand, compress or otherwise fill CCD detector 54. Hence, optics 50 can include a beam compressor, beam expander or other optical elements known in the art. Optics 50 then compresses or expands radiation 18a' and 18b' and outputs that radiation to an image detection and processing unit 52. Image detection and processing unit 52 includes a charge coupled device (CCD) 54 which detects the intensity pattern from radiation 18a' and radiation 18b'. This intensity pattern will include coherent interference signals, i.e., homodyne or heterodyne detection can be achieved, provided the absolute value of the difference between path length $L_R$ and $L_O$ is approximately within the coherence length (CL) of source 12. Image detection and processing unit will be described in more detail with reference to FIG. 8 below. A computer 57 allows a user to control the process of image acquisition performed by image detection and processing unit 52 and displays of resulting images on monitor 59 or stores them on a hard disk (not shown) or some other digital storage device.

Figure 3:
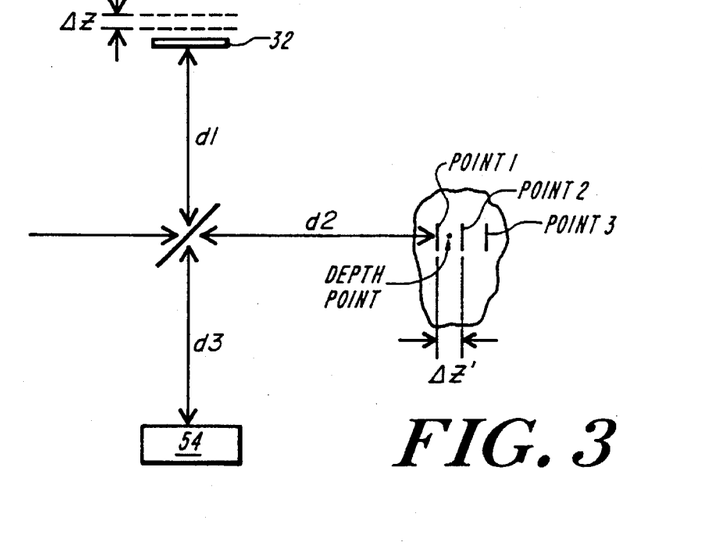
FIG. 3 is a simplified version of the optical paths within the system of FIG. 2.

FIG. 3 is a simplified version of the optical paths within system 10 using a single ray of radiation 17a, 17a', 17b, 17b', 18a', 18b' of FIG. 2. In particular, the path length from splitter 22 to reference scatterer 32 is defined as d1, the path length from splitter 22 to a region 202 to be imaged is defined as d2 and the path length from splitter 22 to CCD detector 54 is defined as d3. Hence, the reference path length $L_R$ discussed above is 2d1+d3 and the object path length $L_O$ is 2d2+d3. Hence, since the absolute value of the difference between $L_R$ and $L_O=|2(d2-d1)|$, if this value is less than or equal to CL, coherent detection occurs.

Coherent or Heterodyne Detection for a Single Ray

When scatterer 32 moves at a velocity V, a Doppler shift frequency having a frequency $f_D=2V/\lambda$ occurs, where $\lambda$ is the nominal wavelength of the radiation output by source 12. When reference radiation 17a' is shifted by this frequency $f_D$ (due to the motion of scatterer 32) and resulting radiation 18a' spatially overlaps object radiation 18b' which did not undergo such a Doppler shift, then the intensity will vary at a "beat" or intermediate frequency equal to $f_D$. This intermediate frequency signal will only occur, however, if radiation 18a' and 18b' coherently interfere with each other which in turn only occurs if the absolute value of the path difference $|L_R-L_O|$ is less than the coherence length CL of source 12 as discussed above. Hence, the above conditions are satisfied, detector 54 can detect and output this intermediate frequency signal. Moreover, when the velocity V is large enough, the resulting Doppler shift $f_D$ will be higher than the predominant low frequency (1/f type) noise spectrum. For an 830 nm wavelength output from source 12, which might be a typical source wavelength, this occurs for a velocity V above approximately 1 mm/sec.

Longitudinal Scanning for a Single Ray

Longitudinal scanning, i.e., scanning in the z direction of object 28, is also achieved as a result of the motion of scatterer 32. Referring again to FIG. 3, path lengths $L_R$ and $L_O$ are initially equal with the beam at a desired initial scan depth in object 28. As scatterer moves away from splitter 22, the point in object 28 at which the path lengths are equal is scanned to successively greater depths within object 28. At each point in the scan, radiation scattering occurs and is a function of optical characteristics of object 28 such as refractive index variations, as well as absorption, scattering and spectral characteristics of object 28 through which radiation 17b' is passing.

Figure 4A:
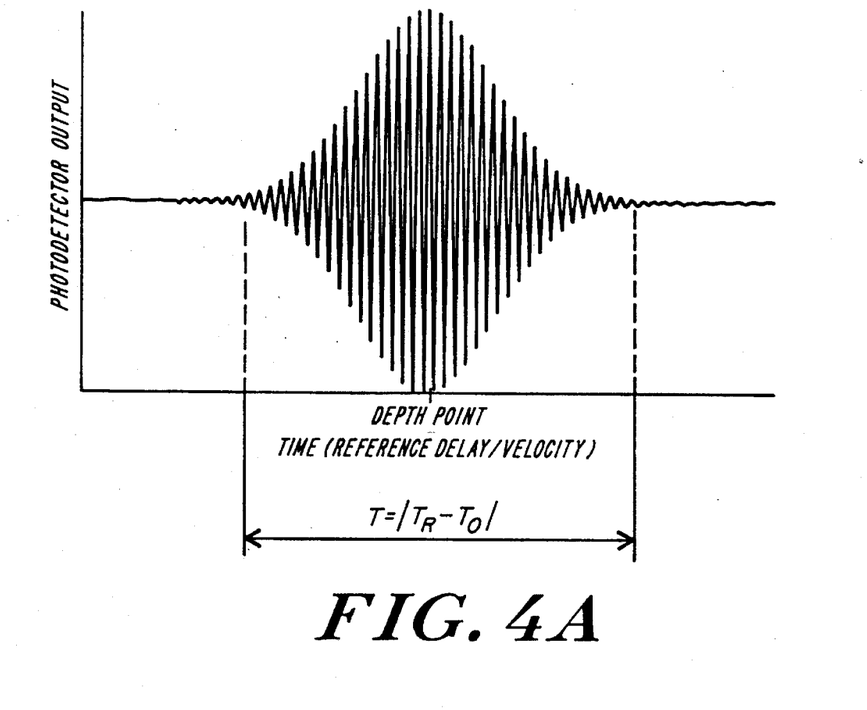
FIG. 4A shows one example of an intermediate frequency signal resulting from coherently detecting an interference pattern produced by overlapping radiation scattered from the reference path and the object path and FIG. 4B shows this same output portion after demodulation.
Figure 4B:
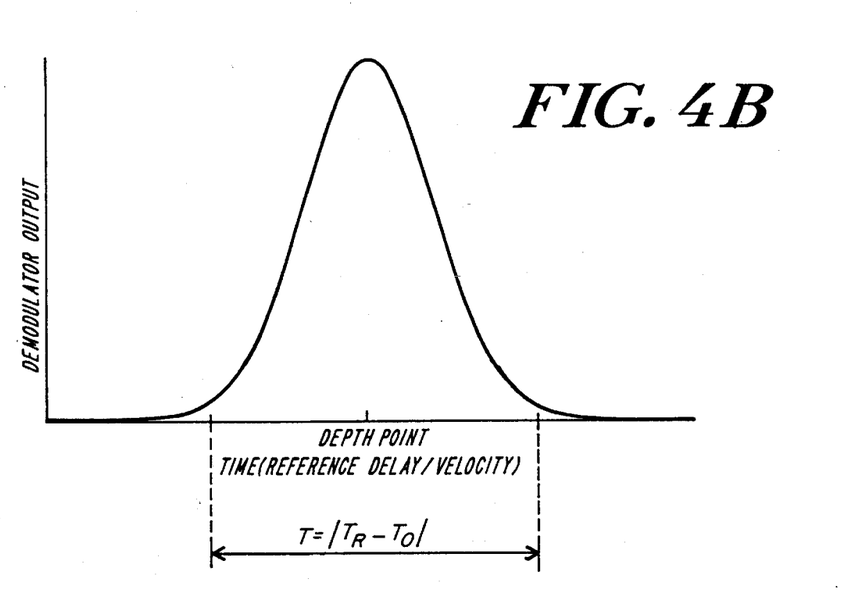

FIG. 4A shows one example of an intermediate frequency signal output by detector 54 for a single scatterer at given depth point (see FIG. 3) in object 28, where the absolute value of the difference between the object path length $L_O$ and the reference path length $L_R$ is less than the coherence length (CL) of the light source (i.e., $|L_O-L_R|<CL$). The intermediate frequency signal appears for a time T which is the absolute value of the difference between the reference delay time $T_R$ and the object delay time $T_O$, i.e., $|T_R-T_O|$. Note that the intermediate frequency signal shown in 4A also has an envelope signal superimposed thereon as discussed in the parent to this application. This envelope signal occurs because as the reference length $L_R$ varies due to the motion of scatterer 32, $|L_R-L_O|$ is scanned through the coherence length CL of source. Consequently, the intermediate frequency signal disappears while $|L_R-L_O|$ sweeps by more than the coherence length CL beyond the depth point. FIG. 4B shows this same output portion after demodulation. A variety of demodulation approaches are discussed in U.S. patent application Ser. No. 07/875,670 which is one of the parent applications to this application.

The above discussion showed that the coherence length CL of source 12 determines available system resolution ($\Delta z'$) in the z direction and the intermediate frequency output from detector 54 is indicative of scattering obtained at a particular depth z within object 28. Consequently, successive interferometric outputs obtained during a scan form profiles of the optical characteristics of object 28. The profiles can be index, scattering (even microstructure scattering), absorption or refractive index profiles within the samples where scattering is normally maximum and may have some lesser peaks in a predetermined pattern, depending on the scattering characteristics of the medium at the scan depth.

In view of the above, it is apparent that it is not just the peak wavelength of source 12 which determines the system longitudinal resolution $\Delta Z'$, but rather the coherence length of source 12 as successive depth points are longitudinally scanned as discussed in the parent to this application. Hence, the higher the desired longitudinal resolution the lower the coherence length CL of source 12. Moreover, the lower the coherence length CL of source 12 the wider the spectral width of radiation output by that source. In addition, the spectral width of many sources with longer coherence lengths such as lasers and light emitting diodes can also be modified using mechanical, electrical modulation and other known techniques.

Parallel Image Capture

Figure 5:
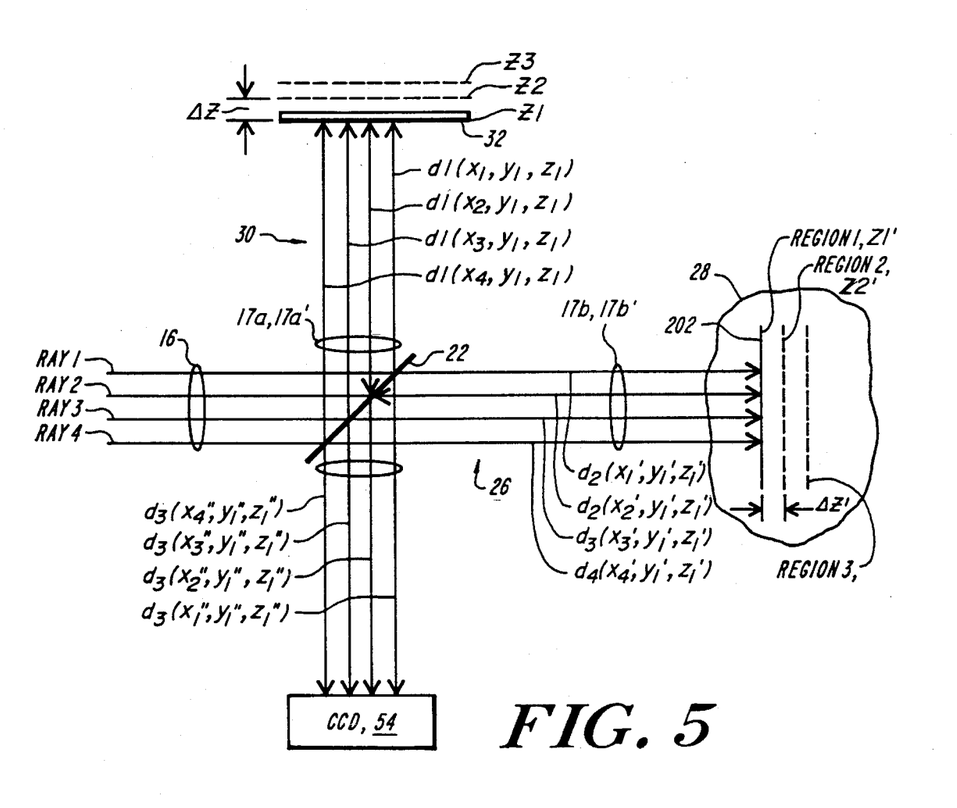
FIG. 5 corresponds to FIG. 3 with spatially expanded radiation 17a, 17a', 17b, 17b', 18a, 18b' as shown in FIG. 2.

FIG. 5 is a simplified depiction of a parallel image capture system which corresponds to FIG. 3 with spatially expanded radiation 17a, 17a', 17b, 17b', 18a', 18b' as shown in FIG. 2. Here, however, four rays, ray 1, ray 2, ray 3 and ray 4 of radiation 16 are shown. FIG. 5 is referred to as simplified, because it depicts rays 1–4 with no crossing or overlapping which in practice occurs to some degree. Again, these rays can be in one or two transverse directions. The path lengths from splitter 22 to reference scatterer 32 are defined as $d1(x_i,y_1,Z_1)$, where i=1, 2, 3 and 4 for rays ray 1, ray2, ray 3 and ray 4, respectively. Similarly, the path lengths from splitter 22 to a region 202 to be imaged are defined as $d2(x_i',y_1',z_1')$ and the path lengths from splitter 22 to CCD detector 54 are defined as $d3((x_i'',y_1'',z_1''))$, where i=1, 2, 3 and 4 for ray 1, ray 2, ray 3 and ray 4, respectively. Hence, the reference path length $L_R$ discussed above is $2d1(x_i,y_1,z_1)+d3(x_i,y_1,z_1)$ and the object path length $L_O$ is $2d2((x_i',y_1',z_1')+d3(x_i,y_1,z_1)$, where i=1, 2, 3 and 4 for ray 1, ray 2, ray 3 and ray 4, respectively. For example, coherent detection (and consequently intermediate frequency $f_D$) for a particular ray—say ray 1—only occurs when the absolute value of the optical path difference $L_R(xi,yj,zk)-L_O(xi',yj',zk')$ for that ray is within the coherence length CL of source 12. Moreover, this must be true for each ray of radiation 18a' and 18b'.

Figure 6A:
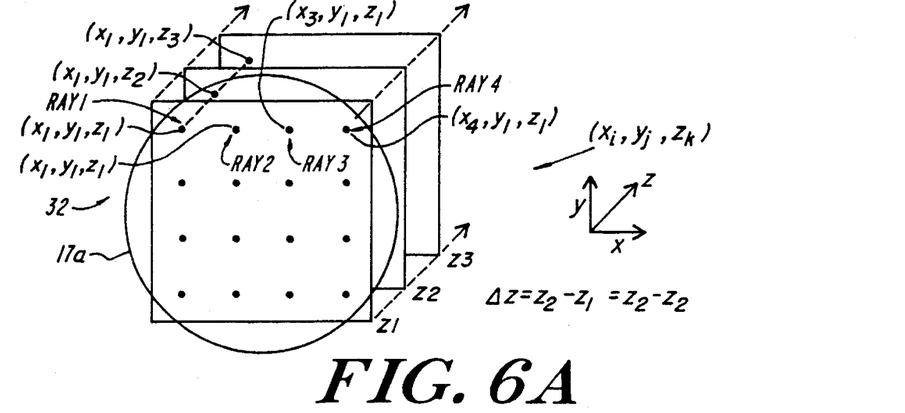
FIGS. 6A, 6B and 6C show a front view of the reference scatterer, a region in the object, and the detecting surface of the detector array, respectively.
Figure 6B:
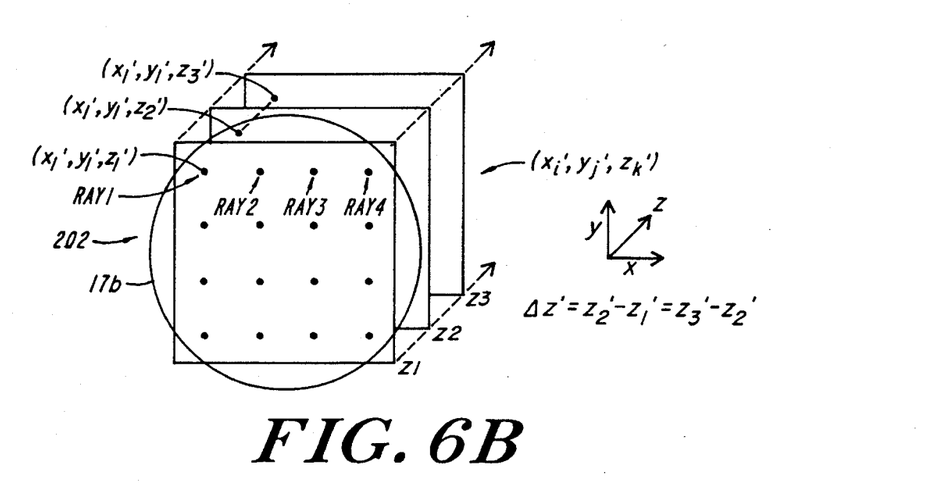
Figure 6C:
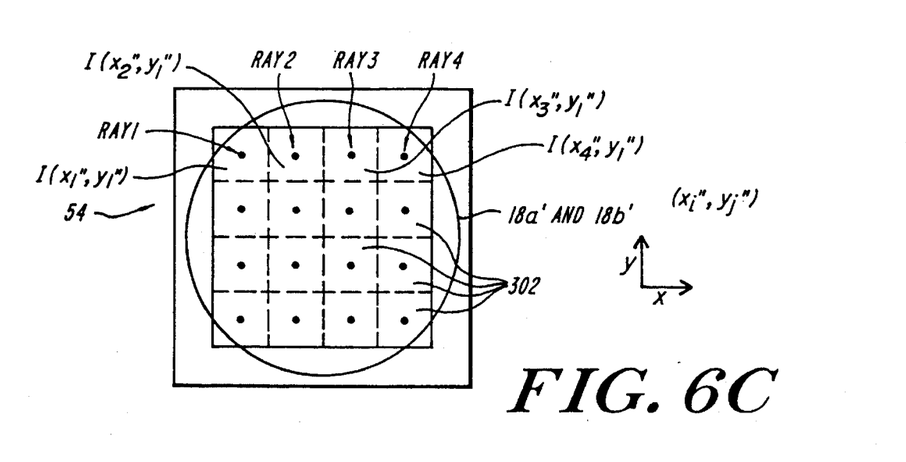

FIGS. 6A, 6B and 6C show a front view of reference scatterer 32, a region 202 in object 28 and detector surface 302 of detector array 54, respectively. The front views are shown in two transverse directions, it being understood that when radiation 16 is elliptical, only one dimension need be shown. In the discussion that follows, radiation in two transverse directions is discussed, however, all aspects of image acquisition in one dimension is analogous to the below discussion of two directions. In addition, the following discussion represents a simplified discussion of the primary processes which take place in parallel image capture, it being understood that there will be crosstalk between rays in the reference or object paths.

FIG. 6A shows ray 1, ray 2, ray 3 and ray 4 which are incident on scatterer 32 at locations (x1,y1,z1), (x2,y1,z1), (x3,y1,z1) and (x4,y1,z1), respectively. The longitudinal position of scatterer 32 is determined by the coordinate z and hence z1, z2 and z3 represent three different longitudinal positions of reference scatterer 32. As scatterer 32 moves toward and away from splitter 22, the longitudinal position z of scatterer 32 changes but the transverse coordinates (xi,yj) of rays 1–4 does not necessarily have to vary.

FIG. 6B shows rays 1, 2, 3 and 4 which are incident on region 202 of object 28 at locations (x1',y1',z1'), (x2',y1',z1'), (x3',y1',z1') and (x4',y1',z1'), respectively. The longitudinal position of region 202 is determined by the coordinate z' and hence z1', z2' and z3' represent three different longitudinal positions of region 202. Moreover, the longitudinal positions z' of region 202 being imaged, changes from z1', z2' and z3', as scatterer 32 changes from z1, z2, and z3, respectively.

FIG. 6C shows rays 1, 2, 3 and 4 which are incident on scatterer 32 on detection elements 302 at locations (x1",y1"), (x2",y1"), (x3",y1") and (x4",y1"), respectively. The number of subregions 302 can range from a few to several thousand depending on the desired spatial resolution $\Delta x'$ and $\Delta y'$ of regions 1, 2, 3 in object 28. $I(x",y")$ is the intensity of radiation incident on element 302 at location $(x",y")$. Moreover, if no ray is scattered from a particular subregion of object 28 no intermediate frequency signal can appear at the element 302 corresponding to that ray. For example, suppose there is no radiation 17b' from ray 1 scattered back from location (x1',y1',z1') of object 28, then there will be no intermediate frequency signal $I(x1",y1")$ detected at the element 302 at location (x1",y1"). In addition, if an intermediate frequency signal does appear at element 302 at location (x1",y1"), then the amplitude of the demodulated signal (see FIG. 4B) provides an indication of the magnitude of the amount of radiation 17b' scattered from location (x1',y1',z1') as a result of ray 1 incident on that subregion. In this manner, a one or two dimensional image of region 1 (a longitudinal slice of object 28) can be acquired in a parallel manner.

Simultaneous capture of an image as discussed above requires that system 10 be properly aligned. This means that a significant portion of radiation 18a' from reference scatterer 32 physically overlaps with radiation 18b' from object 28 to insure that radiation 18a' can interfere with 18b' at CCD detector 54. Note that the cross-sectional view of radiation incident on array surface 302 need not necessarily be the same size as the transverse dimensions of radiation 17a or 17b, because optics 50 can be a beam compressor or beam expander depending whether the transverse dimensions of radiation 18a' and 18b' are to be compressed or expanded before reaching array surface 302.

Longitudinal two dimensional slices are captured in a parallel manner as follows. Referring again to FIGS. 6A–6C, the longitudinal position of scatterer 32 is determined by the coordinate z and hence z1, z2 and z3 represent three different planar longitudinal positions of reference scatterer 32. Similarly, object radiation 17b is incident on object 28 at planar regions 1, 2 and 3 which is a plane determined by longitudinal coordinates z1', z2' and z3', respectively. Now interference fringes occur for depth points in the sample where the absolute value of the difference between the object path length from splitter 22 for a point (xi',yj') in object 28, $L_O(xi',yj')$, and the reference path length for a corresponding point (xi',yj') on reference scatterer 32, $L_R(xi,yj)$, is less than the coherence length (CL) of the light source (i.e., $|L_O(xi',yj')-L_R(xi,yj)|<CL$). Therefore, the coherence length of the light source determines available system resolution in the z direction.

Suppose path lengths $L_R(xi,yj,zk)$ and $L_O(xi',yj',zk')$ for all rays are initially equal at a desired initial scan depth z' in object 28. As scatterer 32 moves away from splitter 22, an entire plane (or line if radiation 16 is elliptical) in object 28 at which the path lengths are equal is scanned to successively greater depths within object 28. At each plane in the scan, radiation scattering occurs and is a function of the refractive index variation for the material through which the radiation is passing and of such index boundaries at each subregion (xi',yj'). The longitudinal scan involved scanning a plane (or line if only one transverse is being used) through object 28. This longitudinal scan is not, however, limited to a plane, but instead can be any two dimensional shape (or one dimensional curve) and it is the shape of scatterer 32 that determines the shape of regions longitudinally scanned through object 28 as will be discussed below.

Coherent or Heterodyne Detection

The heterodyne detection process will now be discussed when subregions (x,y) all move at a single velocity V. When scatterer 32 and its subregions move at a velocity V, a Doppler shift frequency having a frequency $f_D=2$ V/$\lambda$ occurs, where V is the velocity at which scatterer 32 is moved and $\lambda$ is the wavelength of source 12. The Doppler shift frequency $f_D$, is superimposed on the envelope signal as shown for a small portion of an intensity output in FIG. 4A. The envelope signal shown in FIG. 4A will be present at every detecting surface 302 (see FIG. 6C) which receives object scattered radiation 18b' from a corresponding subregion (x,y) on object 28. FIG. 4B shows this same output portion after demodulation. Again, if the velocity V is large enough, the resulting Doppler shift frequency will be above the 1/f type noise spectrum of the system.

Uniform Longitudinal Scanning

Reference scatterer 32 is secured to mechanism 39 (FIG. 2) which moves the scatterer 32 toward and away from splitter 22 in a particular pattern. Referring to the embodiment of FIG. 2, mechanism 39 moves scatterer 32 away from splitter 22 at a uniform, relatively high velocity V. The desired value of velocity V depends on the wavelength of radiation output by source 12. Regardless of the value of velocity V, it is desirable that all subregions (xi,yj) on scatterer 32 move at a single velocity V to ensure that each ray scattered by each subregion (xi',yj') is Doppler shifted by the same frequency $f_D$. In that case, each pixel will have the same intermediate frequency signal (provided object radiation is received from object 28) indicative of the optical characteristics of subregion (xi',yj'). Moreover, each of the subregions (xi',yj') that does have such an intermediate frequency signal can be demodulated in a manner analogous to that discussed above with respect to a single ray system. However, in order to achieve a single intermediate frequency Doppler shift, all subregions (xi,yj) of scatterer 32 must move at a single velocity. This can be achieved in several ways.

In one embodiment, when scatterer 32 reaches the far end of its travel path, scatterer 32 is rapidly returned to the initial position, the scan having a generally ramp or sawtooth profile, with measurements being taken on the ramp. Mechanism 39 may also return scatterer 32 to its initial position at substantially the same rate V, movements of the mirror thus being in a triangular pattern. With a triangular scan, readings or measurements can be taken with scatterer 32 moving in either one of the two directions, or can be taken with scatterer 32 moving in both directions. Mechanism 39 may be any one of a Variety of devices adapted for performing the mirror translation function. For example, mechanism 39 could be a stepper motor, the motion of which is applied to scatterer 32 through an averaging mechanism to provide uniform velocity. A DC servo motor might also be utilized to obtain the desired motion. Various electromagnetic actuators, for example, a speaker coil, may also be utilized for moving scatterer 32. With such electromagnetic actuators, detection of scatterer position and servo-control thereof are also required in order to achieve the desired uniform motion. More specifically, in such a system, a signal indicative of desired scatterer position at each point in the scatterer travel path would be compared against a signal from a detector of actual scatterer position and any resulting error signals utilized to control the actuator to maintain scatterer 32 moving at the desired constant velocity. It would also be possible to use a servo-controlled galvanometer driven linear translator for mechanism 39. One potential problem is that when scatterer 32 is being translated at high speed by mechanism 39, it is nearly impossible to completely eliminate all wobbling of scatterer 32 which may adversely affect the accuracy of distance determinations. Various mechanisms may be utilized to correct for such wobble so that more of radiation 17a is scattered back as radiation 17a' toward splitter 22.

In the above discussion relating to system 10 in FIG. 2, reference unit 31 and in particular mechanism 39 with scatterer 32, can be modified to provide a series of two dimensional images in the transverse direction (or one transverse dimensional images if radiation 16 is elliptical) at a single depth point z. One way to accomplish this is if mechanism 39 vibrates or dithers scatterer 32 back and fourth about a single point z1 at a frequency fm. It should be noted that the vibrating frequency $f_m$ should be selected to be great enough to ensure that the resulting intermediate frequency signal is above the 1/f type noise floor of system 10 and sufficient to prevent aliasing. In addition to dithering, one or more acousto-optic modulators can be used to impose the desired optical frequency offset between the reference and object beam.

As previously discussed, an intermediate frequency signal output from a particular element 302 will be present only if radiation 17b' is scattered from a particular subregion (x',y'). Hence, a two dimensional image can be created by determining which elements 302 at (xi", yj") output an intermediate frequency signal and hence which subregions (xi',yj') scatter radiation 17b'. Moreover, if region z1' physically varies with time so that subregions (xi',yj') may scatter radiation 17b' back towards splitter 22 during one data acquisition time and not scatter radiation 17b' at a later data acquisition time, the resulting two dimensional image will itself change with time. Hence, system 10 used in this mode provides a two dimensional real time monitoring system.

In the above discussion, an additional frequency shift of either radiation 17a, 17a' and/or radiation 18a, 18a' can be introduced by adding modulating units in either path 26 or path 30. In addition, suppose that radiation in path 26 or 30 is shifted by a modulation frequency $F_S$ where $F_S \gg f_m$. The resulting intermediate frequency signal output at each element 302 will be a signal having a carrier frequency $F_S$ and frequency modulated by a signal proportional to $\cos(f_m t)$. If $F_S$ is greater than the noise floor of system, scatterer 32 need not be scanned at high frequencies $f_m$ and still be well above the noise floor.

Figure 7:
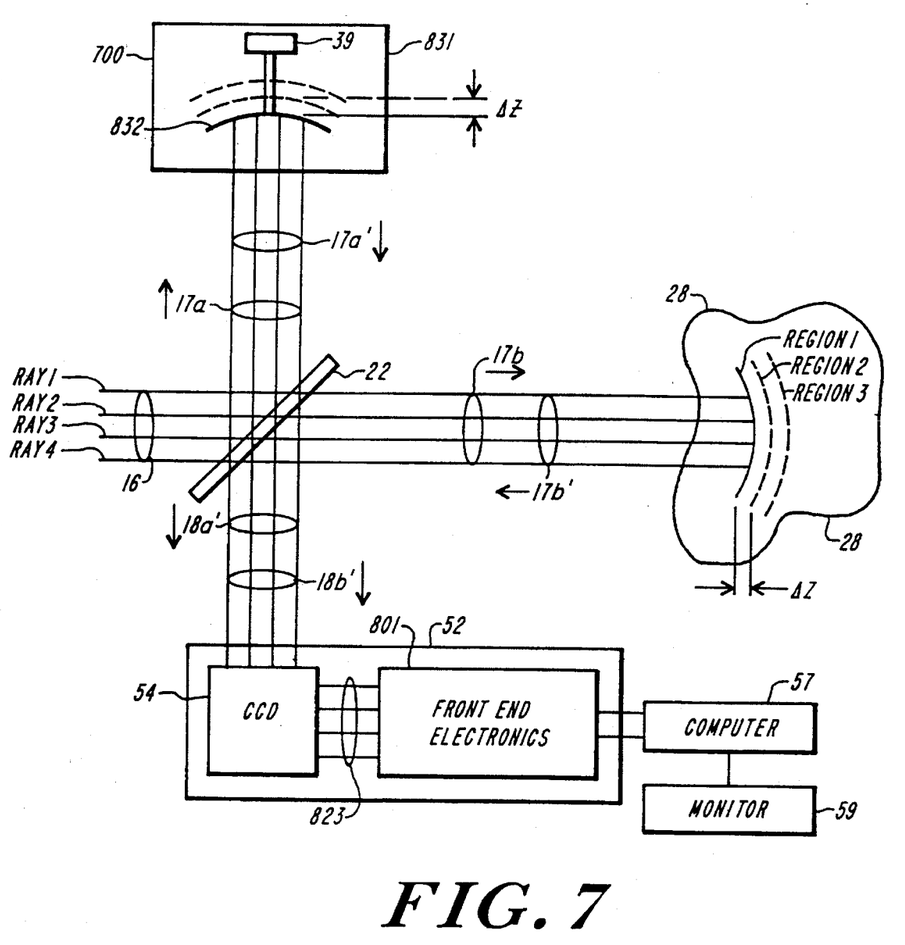
FIG. 7 shows an embodiment in which the reference unit of FIG. 2 has been replaced by an alternate reference unit and, in particular, the scatterer of FIG. 2 has been replaced with a curved scatterer.

FIG. 7 shows an embodiment in which reference unit 31 of FIG. 2 has been replaced by reference unit 830 and, in particular, scatterer 32 has been replaced with a curved scatterer 832. Here, curved scatterer 832 is moved toward and away from splitter 22 as before. However, this motion translates into longitudinally scanning curved regions 1, 2, 3 through object 28. Any other shaped scatterer can be used as scatterer 32 and the shape of that scatter translates into correspondingly shaped regions in object. Consequently, this control over the shape of regions scanned in object 28 can be tailored to the specific application. For example, if 28 represents a human eye, it may be desirable to form scanning regions in the eye with approximately the same curvature as the cornea or lenses in the eye. Also, reflector 832 can be a deformable mirror such as a metal plated piece of rubber the exact shape being either mechanically or electrically controllable, the latter making it possible to modify the shape of the region longitudinally scanned in real time.

Figure 8:
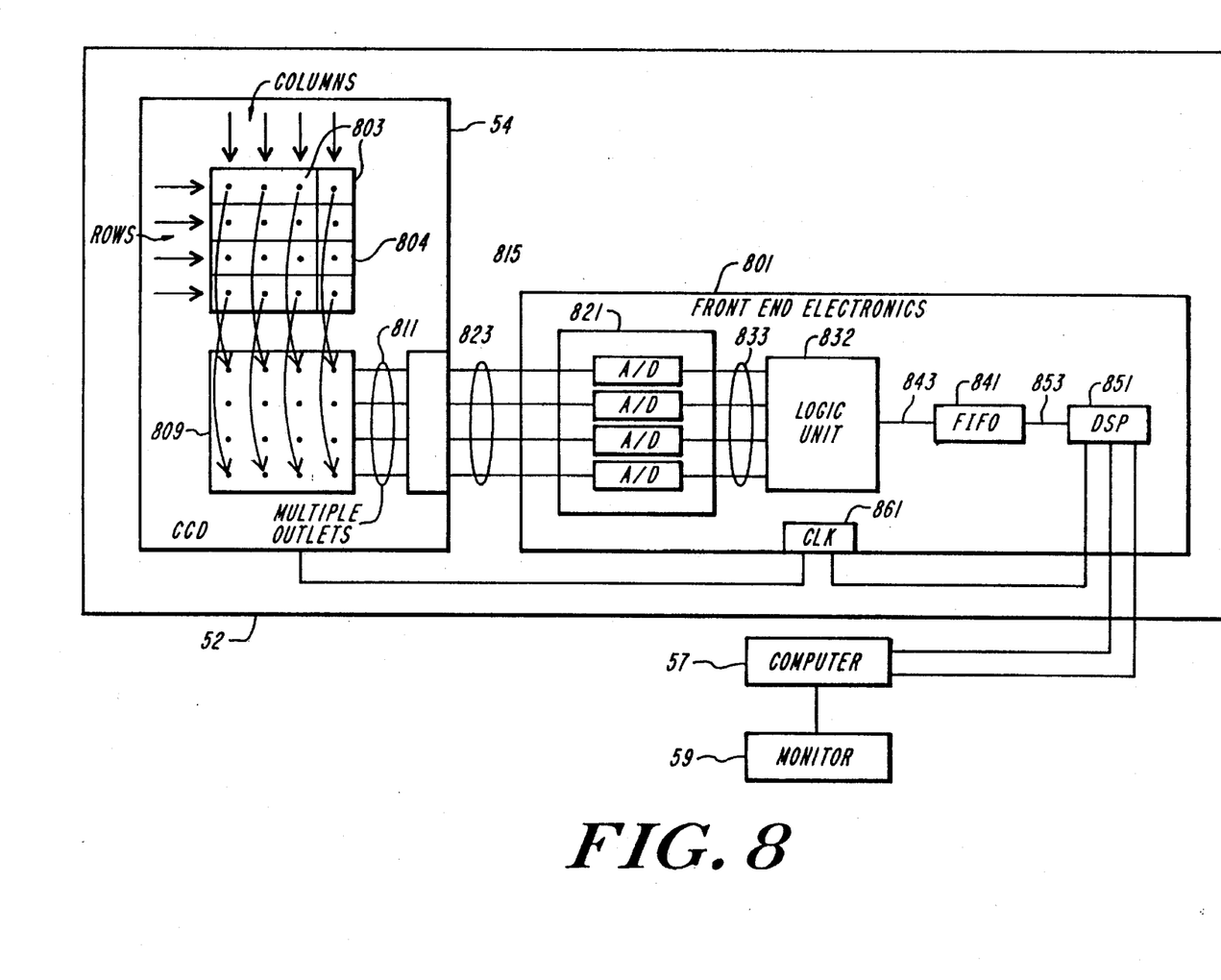
FIG. 8 shows a more detailed schematic representation of image detection and processing unit.

FIG. 8 shows a more detailed schematic representation of image detection and processing unit 52. In particular, image detection and processing unit 52 includes CCD array 54 followed by front end electronics 801. In the preferred embodiment, CCD detector 54 itself includes an imaging area 804, a frame store area 809 and CCD interface unit 815. Front end electronics 801 includes analog-to-digital converters 821, logic unit 832', first-in-first-out (FIFO) unit 841 and digital signal processing unit 851. A system clock 861 provides a synchronizing clock signal to synchronize CCD array 54 with front end electronics 801.

Commercially available CCDs can be used as CCD array 54 and preferably CCD 54 should have a fast frame rate, high quantum efficiency, frame transfer and multiple readouts. A/D converters can also be standard, commercially available A/D converters, preferably having a several MHz conversion rates and at least 12 bit conversion. DSP 851 can be from Texas Instrument's Model TMS 3200 family.

Image detection and processing unit 52 operates as follows. CCD array 54 integrates an intensity pattern on imaging area 804 made of elements 803. Once the image is captured, it is mapped to frame store area 809 to be transferred out of CCD array 54 via interface unit 815. Frame store area 809 is used in order that imaging area 804 can be freed up to capture a new image while frame store area 809 transmits the previous image via interface unit 815 to front end electronics 801. In a preferred embodiment, frame store area 809 has multiple output lines 811 (four such lines are shown but more or fewer are possible) to interface unit 815 which includes buffer amplifiers, double correlated sampling and filtering electronics none of which are shown in FIG. 8 but are known in the art. The resulting signals are then transmitted via lines 823 to analog-to-digital converter 821 which includes parallel analog-to-digital converters 821. Since the rate at which images are transmitted from CCD array 54 largely determines the rate at which images can be acquired, multiple lines 811 and 823 are used to transmit signals from frame store area 809 to front end electronics 801. Consequently, the more output lines frame store area 809 has, the higher the rate at which frames of signals are captured by CCD array 54.

The signals output on lines 823 are respectively analog-to-digitally converted into digital signals which in turn are output to logic unit 832' via respective digital lines 833. Logic unit 832' which rearranges the digital signals into a serial form outputs the data to FIFO 841 via line 843. The digital signals received by FIFO 841 are then output via line 853 to digital signal processor (DSP) 851 in the order they were output from frame store area 809.

Clock 861 synchronizes the rate at which CCD 54 captures and outputs images as well as the rates A/D converters 821 digitize the signals received from CCD 54 as well as the rate at which logic unit 832' filters and outputs data to FIFO 841. The data is then output in the order it was received to DSP 851 which processes the data as follows.

In a most basic implementation, detection unit 52 performs digital signal processing on the received images in a manner analogous to that discussed in the parent applications to this application. In particular, frame capture time is chosen so that there are more than two samples captured per intermediate frequency cycle, which as discussed above, can result from Doppler induced frequency shift, acousto-optic frequency shift, etc, . . . . By sampling more than twice per intermediate frequency cycle, aliasing can be avoided. In the case of uniform velocity scanning, the scanner sweeps the measurement window longitudinally through sample region 202. During this time, a series of samples are recorded for each pixel in FIG. 6C. Thus, a three dimensional data set is captured indicating the optical profiles of the object.

There are numerous real time and non-real time methods to extract information about the optical properties of the sample. In one method, DSP 851 processes sequential samples from the same pixel by digitally band pass filtering around the center frequency followed by digitally rectifying and low pass filtering to remove double frequency terms. Thus, DSP 851 performs a parallel envelope detection operation on the CCD output. Additional filtering can be used to extract and/or compare information (such as cross pixel scattering) from nearby pixels to further increase the utility of the measurements. The processing can involve multiple measurements and averaging to further increase sensitivity. Since the processing is performed digitally, additional information such as phase information can be extracted and/or utilized to improve sensitivity (e.g., improving resolution of the system) as well as provide other useful information. All of the above processing can be done in real time or the digital samples can be stored and then processed later in computer 57.

What is claimed is:

1. An apparatus for acquiring an at least one dimensional image of a region of an object without any transverse scanning, comprising:

a source for outputting radiation having a short coherence length;

means for splitting said radiation into reference radiation and object radiation;

means for receiving said object radiation and directing said object radiation toward the region of the object;

means for receiving said reference radiation and directing said reference radiation through a reference path; and array detecting means for receiving a portion of said object radiation scattered off of said region and a portion of said reference radiation, and for detecting incident intensity in a parallel fashion over said at least one dimension resulting from said portion of said reference radiation coherently interfering with said portion of the object radiation scattered from said region and for outputting a signal corresponding to said incident intensity, wherein said portion of the reference radiation requires a reference delay time to travel from said means for splitting to said array detecting means and said portion of the object radiation requires an object delay time to travel from said means for splitting to said region and then to said array detecting means.

2. The apparatus as claimed in claim 1, wherein said array detecting means comprises a two dimensional array detecting means for receiving said portion of the object radiation and said portion of the reference radiation, for detecting said incident intensity over two dimensions resulting from said portion of said reference radiation coherently interfering with said portion of the object radiation scattered from said region and for outputting said signal corresponding to said incident intensity.

3. The apparatus as claimed in claim 2, wherein said two dimensional array detecting means comprises a charge coupled device.

4. The apparatus as claimed in claim 2, further comprising image processing means for receiving said signal and outputting a two dimensional image corresponding to said region.

5. The apparatus as claimed in claim 2, wherein said two dimensional array detecting means comprises a charge coupled device including a plurality of active detecting areas arranged in rows and columns and a plurality of storage areas also arranged in rows and columns, wherein said plurality of active detecting areas detect said incident intensity and output a first signal to said plurality of storage areas and said plurality of storage areas output said first signal.

6. The apparatus as claimed in claim 5, further comprising a series of analog to digital converters respectively coupled to said rows of the storage areas for receiving and converting said first signal in parallel and outputting corresponding parallel groups of digital data.

7. The apparatus as claimed in claim 6, further comprising a logic unit coupled to said series of analog to digital converters for receiving, filtering and then outputting said groups of digital data as filtered digital data.

8. The apparatus as claimed in claim 7, further comprising a first-in-first-out unit having an input coupled to said logic unit for receiving and storing said filtered digital data and periodically outputting said filtered digital data in block units.

9. The apparatus as claimed in claim 8, further comprising a digital signal processor coupled to said first-in-first-out unit, for receiving said block units and arranging said unit to be displayed as an image.

10. The apparatus as claimed in claim 1, wherein said means for receiving said reference radiation comprises reference path length varying means for varying said reference path, thereby causing said portion of reference radiation to undergo a plurality of reference delay times such that said array detecting means detects a plurality of incident intensities over said at least one dimension and outputs a plurality of signals corresponding to a plurality of regions of said object having a respective plurality of object delay times corresponding to said plurality of reference delay times, respectively.

11. The apparatus as claimed in claim 10, further comprising image processing means for receiving said plurality of signals and outputting a respective plurality of two dimensional images corresponding to said plurality of signals.

12. The apparatus as claimed in claim 11, further comprising three dimensional image processing means for receiving said plurality of signals and outputting a three dimensional image corresponding to said plurality of signals.

13. The apparatus as claimed in claim 12, further comprising a digital signal processing means for receiving said plurality of signals and outputting two dimensional digital images corresponding to said region.

14. The apparatus as claimed in claim 10, further comprising processing means for receiving said plurality of signals and digitally utilizing phase information contained in said plurality of signals.

15. The apparatus as claimed in claim 1, wherein said source outputs said radiation having a coherence length of less than a desired longitudinal resolution.

16. The apparatus as claimed in claim 1, wherein said source outputs said radiation having a peak wavelength in the near infrared spectrum.

17. The apparatus as claimed in claim 1, wherein said source outputs said radiation having a peak wavelength in the near infrared spectrum and a coherence length of less than approximately 10 micrometers.

18. The apparatus as claimed in claim 1, further comprising digital image processing means for receiving said signal and outputting a two dimensional digital image corresponding to said region.

19. The apparatus as claimed in claim 1, wherein said two dimensional array detecting means comprises a charge coupled device including a plurality of active detecting areas arranged in rows and columns and a plurality of storage areas also arranged in rows and columns, wherein said plurality of active detecting areas detect said incident intensity and output a first signal to said plurality of storage areas and said plurality of storage areas output said first signal.

20. The apparatus as claimed in claim 1, wherein said means for receiving said reference radiation and directing said reference radiation through a reference path comprises a scatterer which receives said reference radiation and scatters said reference radiation through the reference path.

21. The apparatus as claimed in claim 20, wherein said scatterer comprises a mirror.

22. The apparatus as claimed in claim 20, wherein said scatterer is curved, thereby causing said region in the object to be similarly curved.

23. An apparatus for acquiring a two dimensional image of a region of an object, comprising:

an optical source for outputting a first optical beam having a short coherence length;

means for splitting said first optical beam into a reference beam and an object beam;

means for receiving said object beam and directing said object beam toward the region of the object and for collecting a portion of said object beam scattered off of said region;

means for receiving said reference beam and directing said reference beam through a reference path; and a two dimensional array detecting means for receiving a portion of said object beam and a portion of said reference beam, for detecting incident intensity over two dimensions resulting from said portion of said reference beam coherently interfering with said portion of the object beam scattered from said region and for outputting a signal corresponding to said incident intensity, wherein said portion of the reference beam requires a reference delay time to travel from said means for splitting to said two dimensional array detecting means and said portion of the object beam requires an object delay time to travel from said means for splitting to said region to said two dimensional array detecting means.

24. The apparatus as claimed in claim 23, further comprising digital image processing means for receiving said signal and outputting a two dimensional digital image corresponding to said region.

25. The apparatus as claimed in claim 23, wherein said two dimensional array detecting means comprises a charge coupled device.

26. The apparatus as claimed in claim 23, wherein said means for receiving said object beam comprises reference path length varying means for varying said reference path thereby causing said portion of reference radiation to undergo a plurality of reference delay times such that said array detecting means detects a plurality of incident intensities over said at least one dimension and outputs a plurality of signals corresponding to a plurality of at least one dimensional regions of said object having a respective plurality of object delay times corresponding to said plurality of reference delay times, respectively.

27. The apparatus as claimed in claim 26, further comprising image processing means for receiving said plurality of signals and outputting a respective plurality of two dimensional images corresponding to said plurality of signals.

28. The apparatus as claimed in claim 27, further comprising digital image processing means for receiving said plurality of signals and outputting a plurality of two dimensional digital images corresponding to said plurality of signals, respectively.

29. A method for acquiring a two dimensional image of a region of an object, comprising the steps of:

outputting radiation having a short coherence length;

splitting said radiation using a splitter into reference radiation and object radiation;

receiving, using an optical guide, said object radiation and directing said object radiation toward the region of the object and for collecting a portion of said object radiation scattered off of said region;

receiving said reference radiation and directing said reference radiation through a reference path;

receiving a portion of said object radiation and a portion of said reference radiation and detecting incident intensity over two dimensions using a two dimensional array detector resulting from said portion of said reference radiation coherently interfering with said portion of the object radiation scattered from said region; and outputting a signal corresponding to said incident intensity, wherein said portion of the reference radiation requires a reference delay time to travel from said splitter to said two dimensional array detector and said portion of object radiation requires an object delay time to travel from said splitter to said region and back to said two dimensional array detector.

30. An apparatus for acquiring an at least one dimensional image of a region of an object without any transverse scanning, comprising:

a source for outputting radiation having a short coherence length;

a splitter which splits said radiation into reference radiation and object radiation and allowing said object radiation to pass toward the region of the object and for collecting a portion of said object radiation scattered off of said region;

a reference scatterer which receives said reference radiation along a reference path and scatters said reference radiation back toward said splitter; and an array detector which receives a portion of said object radiation and a portion of said reference radiation and detects incident intensity in a parallel fashion over said at least one dimension resulting from said portion of said reference radiation coherently interfering with said portion of the object radiation scattered from said region and for outputting a signal corresponding to said incident intensity, wherein said portion of the reference radiation requires a reference delay time to travel from said splitter to said array detector and said portion of object radiation requires an object delay time to travel from said splitter to said region and back to said array detecting means.

31. The apparatus as claimed in claim 30, wherein said array detector comprises a two dimensional array detector which receives a portion of said object radiation and a portion of said reference radiation, detects incident intensity over two dimensions resulting from said portion of said reference radiation coherently interfering with said portion of the object radiation scattered from said region and outputs a signal corresponding to said incident intensity.

32. The apparatus as claimed in claim 30, wherein said scatterer comprises a mirror.

33. The apparatus as claimed in claim 30, wherein said scatterer is curved, thereby causing said region in the object to be similarly curved.

* * * * *

UNITED STATES PATENT AND TRADEMARK OFFICE
CERTIFICATE OF CORRECTION

PATENT NO. : 5,465,147
DATED : November 7, 1995
INVENTOR(S) : Eric A. Swanson

It is certified that error appears in the above-indentified patent and that said Letters Patent is hereby corrected as shown below:

Column 1, line 14, insert --"Governmental Rights"--

Column 1, line 15, insert --This invention was made with government support under Contract No. F19628-90C-0002 by the United States Airforce. The government has certain rights in the invention.--

Signed and Sealed this

Twenty-eighth Day of May, 1996

Attest:

BRUCE LEHMAN

Attesting Officer     Commissioner of Patents and Trademarks